United States Patent [19]

de Buda et al.

[11] 4,372,161

[45] Feb. 8, 1983

[54] PNEUMATICALLY OPERATED PIPE CRAWLER

[76] Inventors: Eric G. de Buda, 55 Humberview Rd., Toronto, Ontario, Canada, M6S 1W7; John R. Boon, 431 Satok Crescent, Milton, Ontario, Canada, L9T 3P2; Michael P. Dolbey, 5 Glen Robert Dr., Toronto, Ontario, Canada, M4B 1J4

[21] Appl. No.: 260,012

[22] Filed: May 4, 1981

[30] Foreign Application Priority Data

Feb. 25, 1981 [CA] Canada ................................. 371711

[51] Int. Cl.³ .......................................... G01N 29/04
[52] U.S. Cl. .................................. 73/432 R; 73/623; 15/104.16; 254/134.6; 376/249
[58] Field of Search ........................... 73/623, 40.5 R; 15/104.16; 254/134.6, 106; 376/249

[56] References Cited

U.S. PATENT DOCUMENTS

| | | | |
|---|---|---|---|
| 2,855,934 | 10/1958 | Daughaday | 254/134.6 |
| 3,224,734 | 12/1965 | Hill | 254/134.6 |
| 3,330,368 | 7/1967 | Baran et al. | 254/134.6 |
| 4,006,359 | 2/1977 | Sullins et al. | 73/623 |
| 4,162,635 | 7/1979 | Triplett et al. | 73/623 |

OTHER PUBLICATIONS

*Nuclear Power*, pp. 1–6, Winter 1978–1979.

Primary Examiner—Stephen A. Kreitman
Attorney, Agent, or Firm—Ridout & Maybee

[57] ABSTRACT

A pneumatically operated pipe crawler for transporting inspection equipment along the interior of a pipe comprises an elongate cylindrical tube of flexible resilient material, such as latex rubber, the tube being partitioned by longitudinally spaced plugs which are hermetically sealed to the wall of the tube thus defining three longitudinally separated chambers. The inspection equipment is mounted at the leading end of the crawler. To advance the crawler along the pipe, air or other gas is supplied to the chambers and exhausted therefrom in repeated cyclic sequence for sequentially expanding the chamber wall portions into clamping relation with the pipe, each wall portion recovering to its axial length upon deflation of the chamber, thereby to propel the tube step by step along the pipe.

9 Claims, 12 Drawing Figures

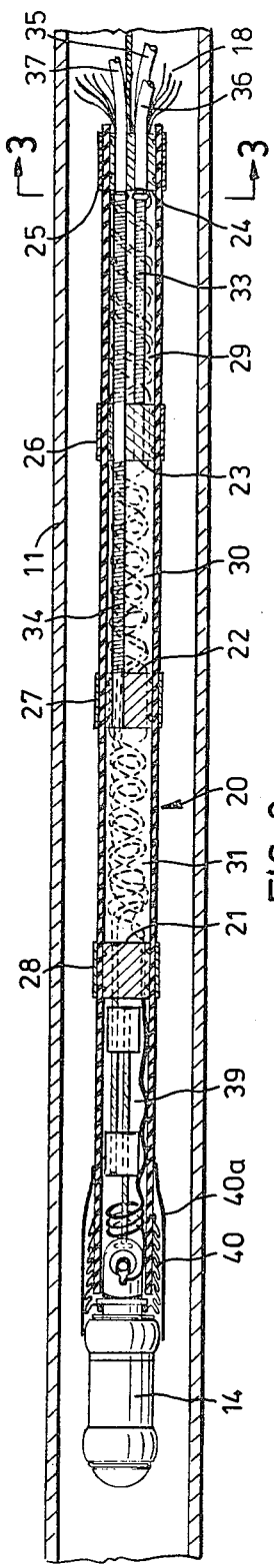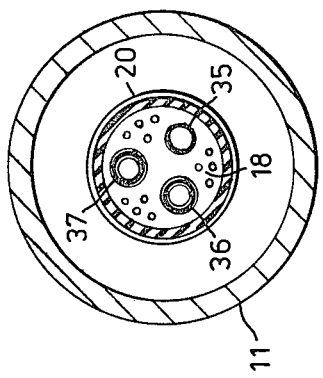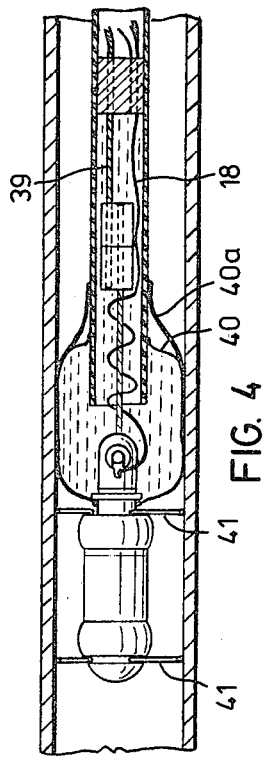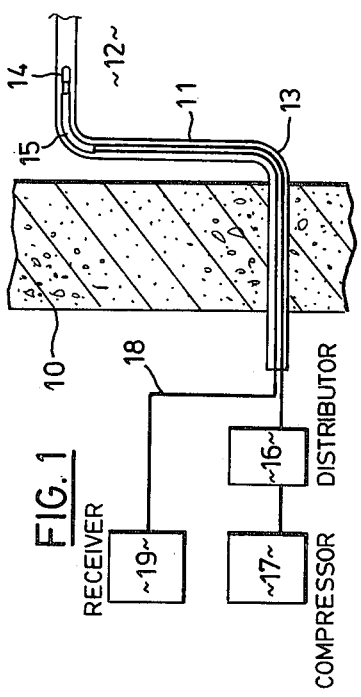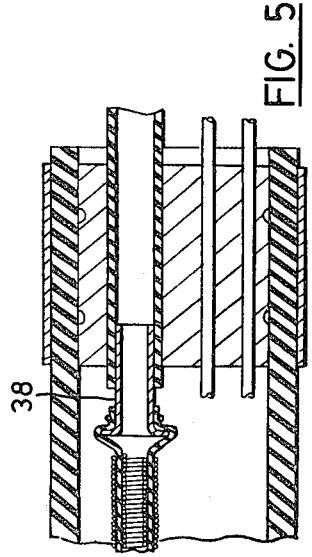

PNEUMATICALLY OPERATED PIPE CRAWLER

This invention relates to a pneumatically operated pipe crawler for use in transporting inspection equipment or repair equipment along the interior of a pipe which otherwise would not be readily accessible.

Self-propelled pipe crawlers operating on the pneumatic principle have been proposed previously. U.S. Pat. No. 3,224,734, for example, describes such an apparatus consisting essentially of three longitudinally separated chambers to which air is supplied, and from which air is exhausted, in cyclic sequence. The leading and trailing chambers have radially expansible walls which are alternately expanded into clamping relation with the interior of a pipe, the intermediate chamber being of telescopic construction and being alternately extended and retracted so as to advance each end of the device alternatively while the other end is secured. This is a well known principle. A serious disadvantage of such an arrangement, however, is that the telescopic intermediate chamber is necessarily rigid and therefore incapable of negotiating sharp bends in pipes such as are encountered, for example, in the water supply pipes of heavy water moderated nuclear reactors.

Instead of making the intermediate chamber of telescopic construction one might in principle employ a bellows. A bellows can be extended and retracted pneumatically, and if suitably dimensioned can negotiate bends in pipe. In practice, however, a bellows construction has been found to be quite unsuitable for the purpose both on account of the nature of its wall and, more important, the fact that the propelling force it can exert is strictly limited.

It is an object of the present invention to provide a pneumatically operated pipe crawler which overcomes these disadvantages and which is suitable for transporting equipment along the interiors of pipes having sharp bends. A characteristic feature of the device is that the wall portions of the chambers are formed by a one-piece tube of flexible resilient material, such as latex rubber for example, the wall portions being radially expansible into clamping engagement with the pipe and each wall portion being recoverable to its original axial length thereby to apply a propelling force which depends upon the elasticity of the material rather than pneumatic considerations alone.

Thus, a pneumatically operated pipe crawler in accordance with the invention comprises: an elongate cylindrical tube of flexible resilient material, the tube having a leading end and a trailing end, support means extending from the leading end of the tube for supporting the inspection equipment ahead of the tube, a plurality of longitudinally spaced partition members located within the tube, said members being hermetically sealed to the wall of the tube and defining therein first, second and third longitudinally separated chambers, each having a radially and axially extensible wall portion, first, second and third flexible gas supply tubes extending from the trailing end of the tube and communicating respectively with said chambers for inflating and deflating the chambers, flexible electrical signalling means extending interiorly of the tube, said signalling means extending from the leading end of the tube for connection to the inspection equipment and extending from the trailing end of the tube for connection to a signal receiver, said gas supply tubes and signalling means being hermetically sealed to the partition members through which they pass, and means for supplying gas to said chambers and exhausting gas therefrom in repeated cyclic sequence for sequentially expanding said chamber wall portions into clamping relation with the pipe, each wall portion recovering to its original axial length upon deflation of the chamber, thereby to propel the tube step by step along the pipe.

One embodiment of the invention will now be described by way of example, with reference to the accompanying drawings, in which:

FIG. 1 is a diagrammatic sectional view of a portion of a nuclear reactor showing the apparatus in use to inspect the interior of a moderator pipe;

FIG. 2 is a longitudinal sectional view of the device positioned with the pipe;

FIG. 3 is a section on line 3—3 in FIG. 2;

FIG. 4 shows a detail of the leading end of the device;

FIG. 5 shows in section a detail of the trailing end of the device; and

Figure 6A:
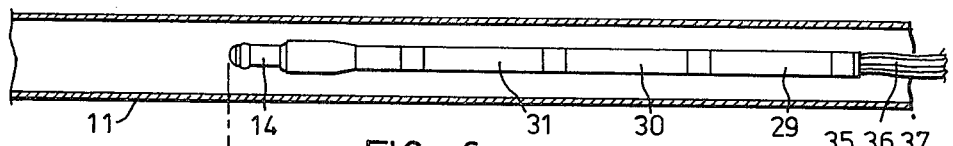
FIGS. 6a–6g are diagrammatic views showing the sequence of operations of the device.

Referring to FIG. 1 there is shown part of a heavy water moderated nuclear reactor having a concrete shielding structure 10 through which a water pipe 11 extends. Within the shielded enclosure 12 the pipe 11 has numerous sharp bends, such as 13, making interior inspection of the pipe particularly difficult. Such inspection may be made using an ultrasonic inspection probe, herein denoted by the reference numeral 14, but the problem is to transport the probe to a region of the pipe which is not readily accessible from the outside. The probe itself, which does not form part of the present invention and will not be described in detail herein, may be of any known type suitable for the purpose, but is preferably of the construction described in the patent application filed concurrently herewith by E. G. de Buda, John R. Boon, and Michael P. Dolbey and entitled "Pneumatically Operated Pipe Crawler".

In FIG. 1 the probe 14 is shown carried by the leading end of the pipe crawler 15, which is shown negotiating a bend in the pipe 11. As the pipe crawler is operated pneumatically, gas supply tubes to the crawler extend through the pipe from a valve distributor 16 connected to an air compressor 17. The valve distributor 16 consists simply of a bank of six valves, one pair for each supply line including a first valve connecting the line to the compressor and a second valve connecting the line to atmosphere, the valves being operated in cyclic sequence for supplying and exhausting air via the air supply tubes for inflating and deflating the chambers of the crawler as hereinafter described. Electrical signals from the probe 14 are transmitted via signalling wires 18 to a receiver 19.

Referring now to FIGS. 2 to 5, the pipe crawler itself comprises a one-piece, elongate, cylindrical tube 20 of flexible resilient material, preferably an elastomeric material such as latex rubber having a high degree of flexibility and resilience as well as being adequately wear resistant. The thickness of the tube wall is such that the tube is self-supporting, i.e. it tends to recover its normal cylindrical shape after being flexed. The interior of the tube is partitioned by four cylindrical metal plugs 21, 22, 23 and 24 to which the wall of the tube is hermetically sealed by being tightly clamped thereon by rigid clamping rings 25, 26, 27, and 28, the material of the tube being pinched between the plugs and clamping rings. The plugs are spaced longitudinally at equal intervals, thus defining three longitudinally separated chambers 29, 30 and 31. Each chamber has a wall portion, constituted by a discrete length of the tube 20, which is both radially and axially extensible for the purpose hereinafter described. For the purpose of inflating and deflating the tube chambers, three polyethylene tubes 35, 36 and 37 are anchored into the rear plug 24 with metal ferrules 38 (FIG. 5) at the trailing end of the tube 20. FIG. 5 illustrates a detail of the structure at the trailing end of the device, but for simplicity the figure shows only the connection to one of the supply tubes. The polyethylene tubes 35, 36 and 37 are flexible and extend rearwardly throughout the pipe 11, being connected at the inlet end to the valve distributor 16. The three polyethylene tubes communicate respectively with the three chambers 29, 30, 31. The metal cylindrical plugs 22 and 23 are formed with through passages for air supply tubes, 33 and 34, communicating with the chambers 30, 31, the tubes being hermetically sealed to the plugs in such passages by a suitable sealant such as Dow Corning RTV Silicone Rubber.

At the leading end of the tube 20 a support for the probe 14 is provided. This support consists of a forwardly extending cable 39 formed by two telescopically arranged parts, one part being connected to the probe 14 at its forward end and the other part extending flexibly along the tube 20. Electrical wires 18 for transmitting power to the probe 14 and transmitting signals from the probe to the receiver 19, as well as a water supply tube and the mechanical cable 39, extend throughout the length of the tube 20, being coiled around the air supply tubes in the chambers through which these tubes extend. These signalling wires, water supply tube and cable 39 are hermetically sealed to the cylindrical plugs through which they pass.

For the purpose of making an inspection within the pipe 11 the probe 14 is extended from the leading end of the tube 20, the mechanical cable support 39 permitting such extension. For this purpose a collapsible bladder 40, covered by a flexible shroud 40a, is mounted at the leading end of the tube 20 and connected to the inspection probe 14 are shown. The bladder is inflated by supplying water under pressure to its interior, by means of the water supply tube referred to above, thereby prising the probe forward. When the bladder 40 is inflated as shown in FIG. 4 the water therein serves as an acoustic medium by which the probe sensor is efficiently coupled to the pipe wall.

As shown in FIG. 4, the probe 14 has radially extending spider arms 41 which can be extended to centre the probe within the pipe 11. This feature does not form part of the present invention and will not be described herein.

Figure 6B:
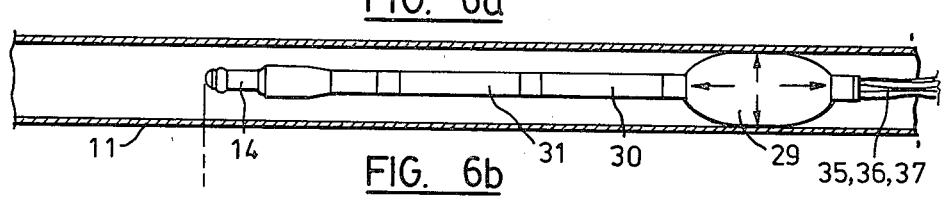
Figure 6C:
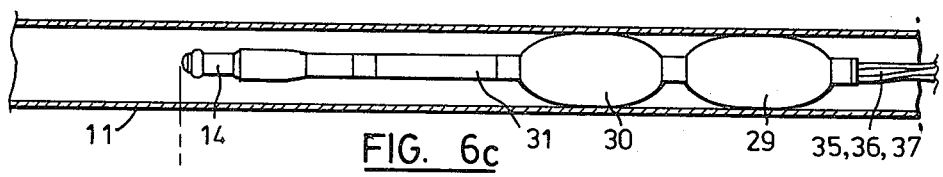
Figure 6D:
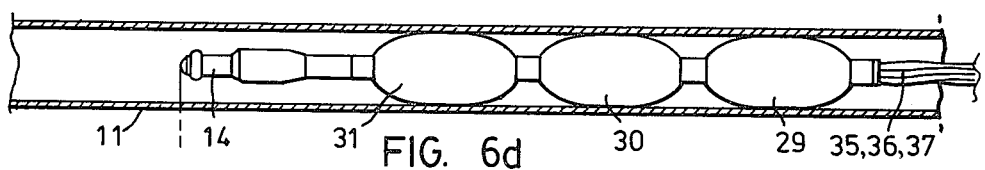
Figure 6E:
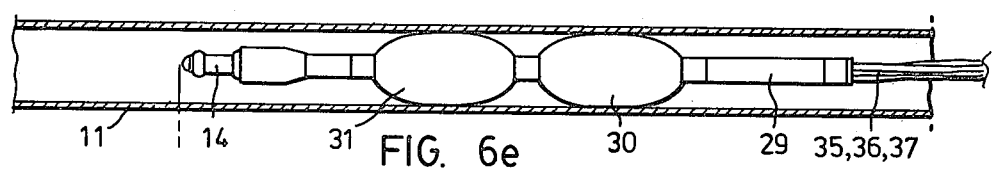
Figure 6F:
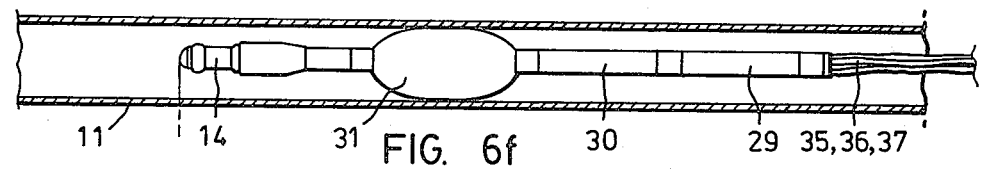
Figure 6G:
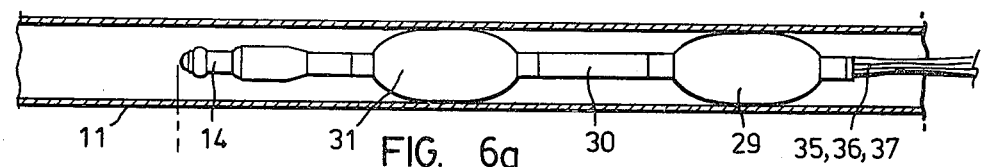

Referring now to FIGS. 6a to 6g, FIG. 6a shows the crawler, with the probe 14 mounted at its leading end, positioned to be advanced along the pipe 11. In this figure the three chambers 29, 30 and 31 are shown deflated. In order to advance the crawler, air is supplied to the chamber 29, thus expanding the wall portion of the chamber into clamping relation with the interior of the pipe as shown in FIG. 6b. However, this expansion also results in axial extension of the chamber 29, the probe 14 being displaced by a small amount to the right. As shown in FIG. 6c, the chamber 30 is next inflated, the chamber 29 remaining inflated and the probe 14 being advanced a step further. Next, as shown in FIG. 6d, the chamber 31 is inflated, causing further advancement of the probe 14, and at this point the wall portions of all three chambers are expanded into clamping relation with the pipe wall. The first chamber 29 is now deflated, as shown in FIG. 6e, the wall portion of the chamber recovering to its normal cylindrical shape. The probe 14 does not move as a result of this, but the trailing end of the crawler advances due to axial contraction of the chamber with recovery of its wall portion. Similarly, the chamber 30 is next deflated as shown in FIG. 6f, causing further advancement of the trailing end of the crawler with the probe 14 remaining in the same position. Next the chamber 29 is inflated, resulting in the shape illustrated in FIG. 6g, and finally, the chamber 31 is deflated, the crawler tube recovering to the original shape shown in FIG. 6b but the probe 14 having advanced by a step. The cycle is repeated to advance the probe 14 by another step, the first stage in the cycle being illustrated in FIG. 6b. The characteristic feature of this cyclic sequence is that the probe 14 is advanced step by step by axial estension of each of the chambers in turn as they are inflated, the trailing end of the crawler being advanced step by step in the second half of each cycle by virtue of the elastomeric recovery of the tube material when the chambers are deflated in turn. This is an important feature, because it means that the traction force exerted by the crawler on the load to be drawn is determined by the elastic strength of the chamber wall portions rather than by pneumatic considerations alone. Moreover as the crawler has a wall which is flexible throughout its length, except for the short lengths of the clamping rings 25, 26, 27 and 28, it can readily negotiate bends in the pipe 11.

What we claim is:

1. A pneumatically operated pipe crawler for transporting inspection equipment along the interior of a pipe, comprising:
    an elongate cylindrical tube of flexible resilient material, the tube having a leading end and a trailing end,
    support means extending from the leading end of the tube for supporting the inspection equipment ahead of the tube,
    a plurality of longitudinally spaced partition members located within the tube, said members being hermetically sealed to the wall of the tube and defining therein first, second and third longitudinally separated chambers each having a radially and axially extensible wall portion,
    first, second and third flexible gas supply tubes extending from the trailing end of the tube and communicating respectively with said chambers for inflating and deflating the chambers,
    flexible electrical signalling means extending interiorly of the tube, said signalling means extending from the leading end of the tube for connection to the inspection equipment and extending from the trailing end of the tube for connection to a signal receiver,
    said gas supply tubes and signalling means being hermetically sealed to the partition members through which they pass, and
    means for supplying gas to said chambers and exhausting gas therefrom in repeated cyclic sequence for sequentially expanding said chamber wall portions into clamping relation with the pipe, each wall portion recovering to its original axial length upon deflation of the chamber, thereby to propel the tube step by step along the pipe.

2. A pipe crawler according to claim 1, wherein the tube is a self supporting tube of elastomeric material.

3. A pipe crawler according to claim 2, wherein said elastomeric material is latex rubber.

4. A pipe crawler according to claim 3, wherein the gas supply tubes are of latex rubber.

5. A pipe crawler according to claim 4, wherein said signalling means are coiled around the gas supply tubes.

6. A pipe crawler according to claim 2, wherein said partition members are cylindrical plugs providing openings for the passage of the gas supply tubes and signalling means, the gas supply tubes and signalling means being hermetically sealed to the plugs at said openings, and the cylindrical tube being clamped to the plugs by clamping rings surrounding the tube.

7. A pipe crawler according to claim 6, wherein the plugs are spaced at equal intervals, said chambers being of the same axial length when deflated.

8. A pipe crawler according to claim 2, said support means being carried by the partition member nearest the leading end of the tube and being extensible therefrom for extending the inspection equipment from said leading end.

9. A pipe crawler according to claim 2, said support means comprising a forwardly extending telescopically extensible cable extending from the partition member nearest the leading end of the tube, and means for extending the cable comprising a collapsible bladder mounted at said leading end and connected to the inspection equipment, and fluid supply means communicating with the bladder for inflating and collapsing same.

* * * * *